United States Patent [19]

Hernandez

[11] Patent Number: 4,840,185
[45] Date of Patent: Jun. 20, 1989

[54] BLOOD SAMPLING DEVICE WITH SHIELD

[76] Inventor: Manuel Hernandez, 1030 NW., 181 St., Miami, Fla. 33169

[21] Appl. No.: 157,274

[22] Filed: Feb. 17, 1988

[51] Int. Cl.⁴ .............................................. A61B 5/00
[52] U.S. Cl. .................................. 128/763; 128/770; 604/198; 604/263
[58] Field of Search ................. 128/763, 770; 604/51, 604/52, 187, 272, 403, 411, 415, 192, 197, 198, 263

[56] References Cited

U.S. PATENT DOCUMENTS

| | | | |
|---|---|---|---|
| 3,244,172 | 4/1966 | Brown | 604/51 |
| 3,987,940 | 10/1976 | Tischlinger | 604/187 |
| 3,993,063 | 11/1976 | Lamabee | 604/187 |
| 4,185,619 | 1/1980 | Reiss | 604/187 |
| 4,398,544 | 8/1983 | Nugent et al. | 128/763 |
| 4,425,120 | 1/1984 | Sampson et al. | 604/198 |
| 4,592,744 | 6/1986 | Jagger et al. | 128/763 |
| 4,643,199 | 2/1987 | Jennings et al. | 128/763 |
| 4,664,128 | 5/1987 | Lee | 604/187 |
| 4,693,708 | 9/1987 | Wandeser et al. | 604/263 |
| 4,723,943 | 2/1988 | Spencer | 604/198 |

Primary Examiner—Max Hindenburg
Attorney, Agent, or Firm—Malin, Haley & McHale

[57] ABSTRACT

A protective shield for a syringe and vacuum tube holder wherein the barrel of either instrument is provided with helical grooves, locking grooves and locking detents. The shield is provided with internal buttons which engage the helical grooves and permit longitudinal movement of the shield into a locked rearward or use position or moved forward into a protective position wherein a needle assembly projecting from the barrel is prevented from accidentally coming into contact with the user.

12 Claims, 2 Drawing Sheets

BLOOD SAMPLING DEVICE WITH SHIELD

BACKGROUND OF THE INVENTION

In the medical field, due to its very nature, there is an extensive amount of daily handling of syringes resulting from injections and also the handling of vacuum tube holders which are used in the many blood sampling procedures carried out by doctors, nurses, technicians and other medical personnel in the many labs, doctor's offices, clinics, hospitals and the like throughout the world.

As a result of this frequent handling of syringes and vacuum tube holders there is a substantial risk that the person handling these instruments will, in fact, sooner or later accidentally stick himself or be accidentally stuck by a coworker with the needle portion which may or may not be contaminated with some highly infectious disease such as Hepatitis or the more feared AIDS virus.

SUMMARY OF THE INVENTION

In view of the seriousness of the above noted potential problem, applicant has undertaken to design a syringe barrel and a vacuum tube holder barrel which is provided with either longitudinal or helical grooves in the outer surface of the barrel which extend the full length of the barrel. Inwardly of each end of the barrel, but adjacent thereto, is a circumferential locking groove in the barrel's outer surface.

A hollow protective shield is telescopically received over the barrel. The protective shield is provided with a first and second pair of spaced buttons projecting from the inner circumferential surface of the protective shield. The first end of protective shield is open to permit placing it over the barrel while the second has an end wall provided with a centrally located aperture to permit the needle and needle holder assembly to project therethrough when said protective shield is in its retracted position to permit use of the syringe or vacuum tube holder. As the protective shield is rotated, the protective shield follows the helical grooves and travels into its retracted position. As it approaches the end of its longitudinal travel the first pair of projecting buttons enters one of the locking grooves and simultaneously the second pair of projecting buttons has entered the second locking groove. At this point, further rotation of the protective shields results in the projecting buttons travelling circumferentially in their respective locking grooves, after approximately ninety degrees of rotating the projecting buttons will drop into a recessed portion of the locking grooves and the protective shield will be "locked " in its retracted position.

Rotation of the protective shield in the opposite direction releases the buttons and further rotation returns the buttons to the helical groove whereupon additional rotation results in the forward travel of the protective shield until the first set of buttons reaches the second locking groove at which time, further rotation results in the protective shield "locked" in its extended or needle projecting position and prevents any contact with the needle.

OBJECTS OF THE INVENTION

An object of the invention is to provide a syringe barrel which is provided with a shield for preventing accidental needle sticking.

A further object of the invention is the provision of a vacuum tube holder barrel which is provided with a shield for preventing accidental needle sticking.

Another object of the invention is the provision of a syringe or vacuum tube holder having shield means which can be locked in its fully extended or fully retracted position.

Yet another object of the invention is the provision of a syringe or vacuum tube holder having a shield which is easily converted from a non-use to a use position.

A further object of the invention is to provide a syringe or vacuum tube holder having a needle protecting shield which is lightweight and inexpensive to manufacture.

A still further object of the invention is to provide a syringe or vacuum tube holder and a protecting shield which are marketed in sterile packaging and disposable after use.

These and other objects of the invention will become more apparent hereinafter. The instant invention will now be described with particular reference to the accompanying drawings which form a part of this specification wherein like reference characters designate corresponding parts throughout the several views.

DETAILED DESCRIPTION OF THE DRAWINGS

Figure 1:
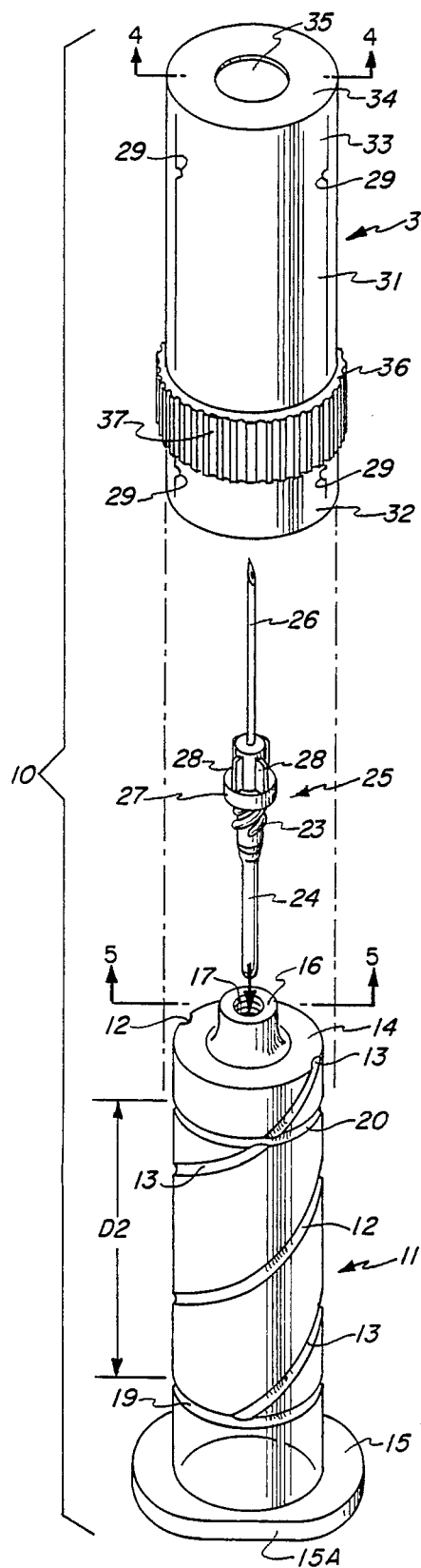
FIG. 1 is a disassembled view of a vacuum tube holder, needle assembly and the protective shield.

Referring now to FIG. 1, there is shown, in a disassembled state, a vacuum tube holder, needle assembly and protective shield all generally indicated by reference numeral 10. The assembly 10 comprises a vacuum tube holder barrel 11 which includes a pair of helical grooves 12 and 13 which begin at forward end wall 14. Helical grooves 12 and 13 extend from forward end wall 14 to rear locking groove 19. Vacuum tube holder barrel 11 is further provided with a forward extension 16 extending from forward end wall 14. A centrally located bore 17, having threads 18 therein, extends through forward extension 16 into the hollow portion of barrel 11. A short distance beyond rear locking groove 19 is an elongated flange 15 which is used when handling the device.

Directly above barrel 11 and forward of extension 16 is needle assembly 25. As shown needle assembly 25 comprises a needle 26 extending from a circular base portion 27. Base portion 27 is provided with vanes 28 that are engaged by one's fingers when inserting threaded portion 23 into threads 18. Projecting downward from threaded portion 23 is extension 24 which projects into barrel 12 when needle assembly 25 is mated therewith.

Positioned directly above needle assembly 25 is protective shield 30. As shown protective shield 30 comprises a cylindrical portion 31 which is open at its lower end 32. Upper end 33 is provided with an end wall 34 having a central opening 35 therein. Adjacent to lower end 32 is a raised band 36 which extends over the full circumference of cylindrical portion 31. Raised band 36 is provided with closely spaced ridges 37 which are gripped by the user's fingers when extending or retracting shield 30 relative to barrel 11. Shown in dotted lines are four projecting buttons 29 which are integral with the inner wall of cylindrical portion 31. As illustrated, buttons 29 adjacent lower end 32 are spaced 180 degrees apart from each other with buttons 29 at upper end 33 also spaced 180 degrees apart from each other. Buttons 29 on the left side of shield 30 are in alignment with each other while buttons 29 on the right side of shield 30 are in alignment with each other. The location of buttons 29 is important and the reason for this will be explained when describing how the shield is "locked" relative to barrel 11.

Figure 2:
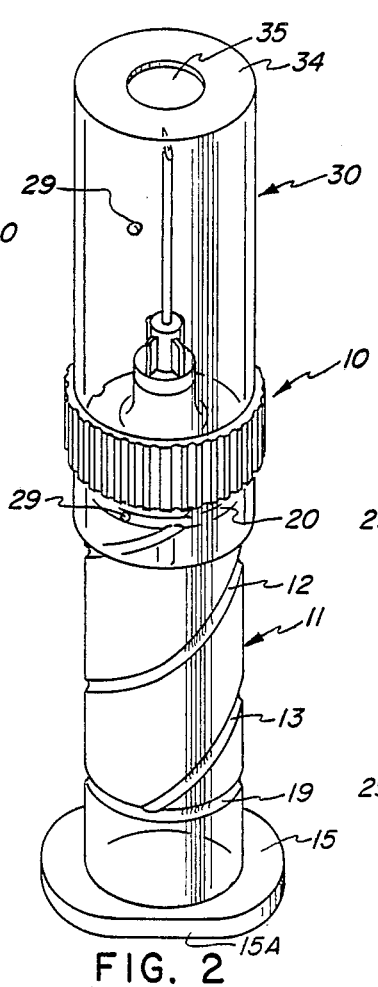
FIG. 2 is an assembled view of the components with the protective shield in its extended locked position.

Referring now to FIG. 2, there is shown the vacuum tube holder 11, needle assembly 25 and protective shield 30 in their assembled state with protective shield 30 in its forward or protective position.

Figure 3:
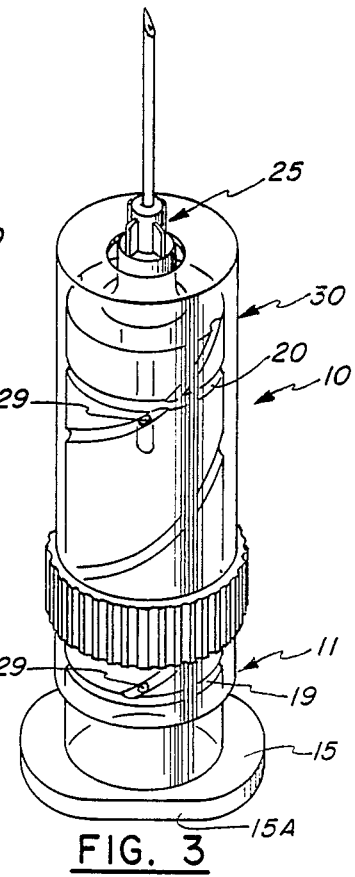
FIG. 3 is an assembled view of the components with the protective shield in its retracted locked position.

FIG. 3 is an illustration similar to FIG. 2 only here, protective shield is in its retracted position permitting use thereof. The shield 30 is "locked" in place by buttons 29 engaging detents 19A and 20A in locking grooves 19 and 20, respectively.

Figure 4:
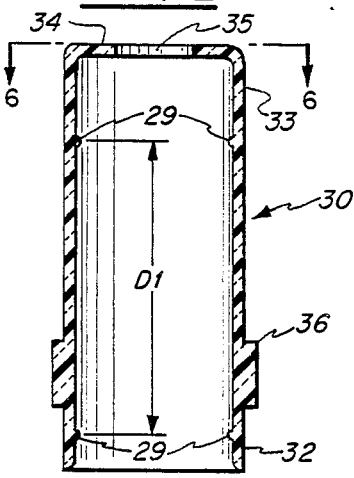
FIG. 4 is a sectional view of the protective shield taken on the plane 4—4 of FIG. 1.

Referring now to FIG. 4, there is shown a sectional view of protective shield 30 wherein the location of projecting buttons 29 is clearly shown. It is to be noted that axial distance $D_1$ is the same as the distance $D_2$ between locking grooves 19 and 20. The reason for this is to permit buttons 29 to be simultaneously rotated into both locking grooves 19 and 20, then ito detents 19A and 20 to "lock" shield 30 in its retracted position.

Figure 5:
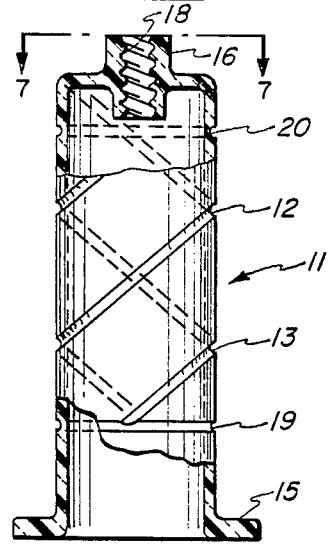
FIG. 5 is a sectional view of the vacuum tube holder taken on the plane 5—5 of FIG. 1.

Referring now to FIG. 5, is shown a sectional view taken on the plane 5—5 of FIG. 1. FIG. 5 clearly shows the location of locking grooves 19 and 20 and also the interior of barrel 11.

Figure 6:
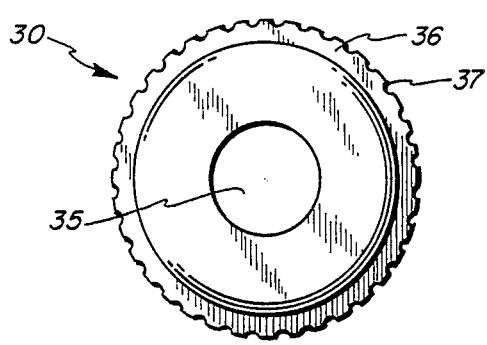
FIG. 6 is an end view of the protective shield taken on the plane 6—6 of FIG. 4.

Referring now to FIG. 6 which is an end view looking down of shield 30 as indicated in FIG. 4. It merely illustrates the concentricity of shield 30.

Figure 7:
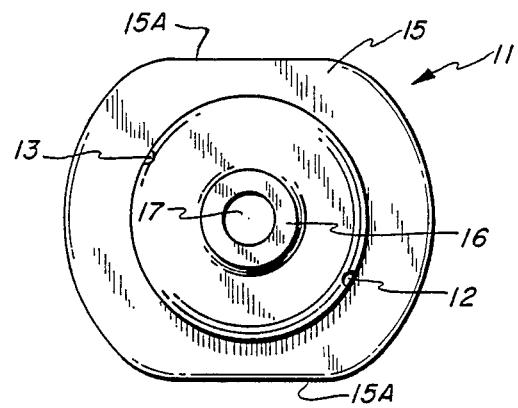
FIG. 7 is an end view of the vacuum tube holder taken on the plane 7—7 of FIG. 5.

Referring now to FIG. 7 which is an end view taken on tha plane 7—7 of FIG. 5. Flange 15 is clearly shown as well as flats 15A. The purpose of flats 15A on opposite side of flange 15 is to prevent entire assembly 10 from rolling off a table or counter onto the floor. The diametrical location of helical grooves 12 and 13 is also illustrated therein.

Figure 8:
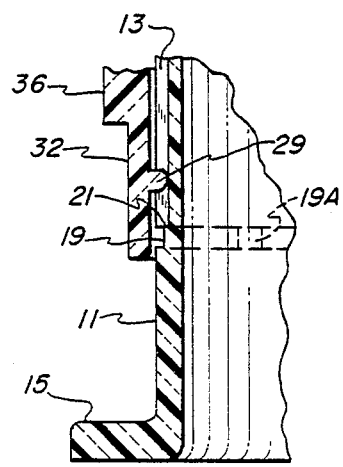
FIG. 8 is a sectional view of the shield as it approaches the locking grooves.

Referring now to FIG. 8, there is shown a sectional view illustrating button 29 in helical groove 13 as it approaches rear locking groove 19. Also shown is a slight shoulder 21 which will be contacted by button 19 as it continues down helical groove 13. When button 19 reaches shoulder 21 an additional rotation is required to force button 19 up into locking groove 19. Once button 19 has entered locking groove 19, slight further rotation will rotate shield 30 sufficiently to permit button 29 to drop into detent 19A.

Figure 9:
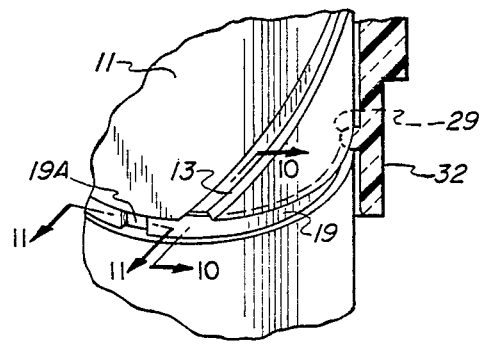
FIG. 9 is a partial sectional view illustrating the projecting button in the locking groove.

Referring now to FIG. 9 there is shown a partial sectional view taken approximately 180 degrees from the illustration of FIG. 8. It must be remembered that there are two buttons 29 at each end of shield 30. FIG. 9 is taken on the other side of barrel 11 and shield 30. As shown in FIG. 9, button 29 has left helical groove 13, climbed over shoulder 21 and entered locking ring 19. Once this has occurred with one button 29, it has simultaneously occurred with all four buttons 29 and all four buttons 29 are now in the locking grooves 19 and 20. The two rearward buttons 29 are in locking groove 19 and the two forward buttons 19 are in the forward locking groove 20. As shown, shield 30 was rotated slightly to left, however, if it were rotated further to the right button 29 would have dropped into detent 19A. As pointed out before, all four buttons 29 are undergoing the same procedure simultaneously. Thus all four buttons 29 would have rotated simultaneously into their respective detents 19A and 20A and shield 20 would be in its "locked" retracted position.

Figure 10:
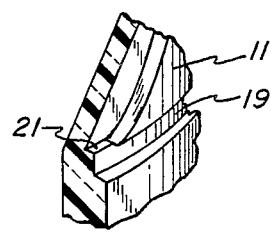
FIG. 10 is a sectional view taken on the plane 10—10 of FIG. 9.

Referring now to FIG. 10 there is a sectional view taken along the line 10—10 of FIG. 9. Here, shoulder 21 is clearly shown as is its relationship to locking groove 19.

Figure 11:
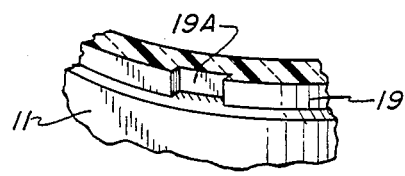
FIG. 11 is a sectional view taken on the plane 11—11 of FIG. 9.

Referring now to FIG. 11, there is shown a detail view of detent 19A. Detent 19A receives button 19 and serves to lock it and shield 30 relative to barrel 11.

A review of the assembly of shield 30 onto barrel is as follows: Shield 30 is aligned to barrel 11 with rearward buttons 29 aligned with the forward end of helical grooves 12 and 13 in forward wall 14 of barrel 11. As buttons 29 enter helical grooves 12 and 13, right-hand rotation of shield 30 with barrel 11 held stationary results in shield 30 rotating and moving longitudinaly over barrel 11 until buttons 29 reach shoulder 21. It should be kept in mind that just prior to this occurring, buttons 29 at the forward end 33 of shield will have become aligned with grooves 12 and 13 at the forward end wall 14 and entered the grooves. When further rotation forces buttons 29 at the rearward end of shield 30 into rearward locking groove 19, forward buttons 29 will also have entered forward locking groove and slight additional rotation will bring all four buttons 29 in their respective detents 19A and 20A and "lock" shield 30 relative to barrel 11.

Another important aspect to be kept in mind is the fact that although the shield 30 has been described in conjunction with a vacuum tube holder, the inventive concept is equally applicable to a syringe wherein the barrel of the syringe is provided with the required helical grooves, locking grooves and detents.

Further, although helical grooves 12 and 13 are utilized herein, a pair of longitudinal grooves spaced 180 degrees apart with a forward and rearward locking groove and appropriate detents would work as well.

While the invention has been described in its preferred embodiments, it is to be understood that words which have been used are words of description rather than limitation and that changes may be made within the purview of the appended claims without departing from the full scope or spirit of the invention.

Having thus described my invention, I claim:

1. A medical device comprising barrel means including an elongated cylindrical portion having a first and second end portion at opposite ends thereof; needle assembly means projecting from said second end portion of said elongated cylindrical portion; groove means provided in the outer surface of said elongated cylindrical portion and protective shield means including locking button means operatively connected to said groove means, said groove means including a plurality of rearwardly extending grooves and a plurality of circumferential locking grooves, said locking grooves located adjacent said first and second end portions of said elongated cylindrical portion, said circumferential locking grooves being intersected by said rearwardly extending grooves with said locking groove being of lesser depth at said point of intersection, whereby said protective shield means is telescopically positioned over said elongated barrel means and is movable between a first and second position to alternatively prevent accidental contact with said needle assembly or permit use of said medical device for its intended purpose.

2. A medical device as set forth in claim 1 wherein said barrel means is the barrel of a vacuum tube holder and used in blood collection.

3. A medical device as set forth in claim 1 wherein said barrel means is the barrel of a syringe and used in injections.

4. A medical device as set forth in claim 1 wherein said second end portion of said elongated cylindrical portion includes a centrally located opening and said needle assembly means is received therein.

5. A medical device as set forth in claim 1 wherein said rearwardly extending grooves are helical and extend from said second end portion of said elongated cylindrical portion to said circumferential locking groove adjacent said first end portion.

6. A medical device as set forth in claim 1 wherein said rearwardly extending grooves are straight longitudinal grooves extending from said second end portion of said elongated cylindrical portion to said circumferential locking groove adjacent said first end portion.

7. A medical device as defined in claim 1 wherein said locking grooves are provided with detent means for receiving said locking button means on said protective shield means to lock said shield means in either of said first and second positions.

8. A medical device as defined in claim 1 wherein said protective shield means comprises an elongated cylindrical body portion having a first open end and a second end having a wall thereacross with a centrally located aperture therein; said locking button means located on the internal surface of said elongated cylindrical body portion; said locking button means cooperating with said pair of circumferential locking grooves to lock said protective shield means in said second position whereby said medical device can be used for its intended purpose.

9. A medical device as set forth in claim 8 wherein said locking button means comprises a first and second pair of locking buttons, said first pair of buttons located near said first open end of said elongated cylindrical body portion and said second pair of locking buttons located near said second end of said elongated cylindrical body portion, one locking button of each pair of locking buttons positioned one hundred and eighty degrees circumferentially from the other locking button of each pair of locking buttons, said first pair of locking buttons being in axial alignment with said second pair of locking buttons.

10. A medical device as set forth in claim 8 wherein said elongated cylindrical body portion of said protective shield means is further provided with a raised band portion extending radially from said elongated cylindrical body portion, said raised band portion having ridges therein to increase the friction when rotated by a user.

11. A medical device as defined in claim 1 wherein said first end portion of said barrel means is provided with flange means projection radially therefrom.

12. A medical device as defined in claim 11 wherein said flange means includes a pair of parallel flat surfaces to prevent rolling of said medical device when said medical device is placed longitudinally on a flat planar surface.

* * * * *